United States Patent [19]

Nonoyama et al.

[11] Patent Number: 5,480,782
[45] Date of Patent: *Jan. 2, 1996

[54] PROCESS FOR OBTAINING CELLULAR PROTEIN HAVING ANTI-HIV ACTIVITY

[75] Inventors: Meihan Nonoyama, St. Petersburg; Akiko Tanaka; Patrick K. Lai, both of Clearwater, all of Fla.

[73] Assignee: Tampa Bay Research Institute, St. Petersburg, Fla.

[*] Notice: The term of this patent shall not extend beyond the expiration date of Pat. No. 5,346,988.

[21] Appl. No.: 285,437

[22] Filed: Aug. 4, 1994

Related U.S. Application Data

[63] Continuation of Ser. No. 659,564, Feb. 22, 1991, Pat. No. 5,346,988, which is a continuation-in-part of Ser. No. 540,973, Jun. 20, 1990, abandoned.

[51] Int. Cl.[6] .................... A61K 38/17; C12P 21/00
[52] U.S. Cl. .................... 435/70.3; 435/70.4; 514/21
[58] Field of Search .................... 314/2, 12, 21; 530/300, 350; 435/70.1, 70.3, 70.4, 70.5

[56] References Cited

U.S. PATENT DOCUMENTS

| | | | |
|---|---|---|---|
| 4,683,199 | 7/1987 | Palladino et al. | 435/172.2 |
| 5,039,794 | 8/1991 | Wier et al. | 530/399 |
| 5,236,829 | 8/1993 | Farber | 530/351 |
| 5,346,988 | 9/1994 | Nonoyama et al. | 530/300 |

FOREIGN PATENT DOCUMENTS

| | | |
|---|---|---|
| 0143850 | 6/1985 | European Pat. Off. . |
| 0193032 | 3/1986 | European Pat. Off. . |
| 0296626 | 12/1988 | European Pat. Off. . |
| 0310056 | 4/1989 | European Pat. Off. . |
| 2146645 | 4/1985 | United Kingdom . |

OTHER PUBLICATIONS

Date stamp pages of AIDS Research and Human Retroviruses, vol. 6, No. 2 (1990).
AIDS Research and Human Retroviruses, vol. 6, No. 2, issued 1990, Lai et al, "Modification of Human Immunodeficiency Viral Replication . . .", pp. 205–217.
Antimicrob, Agents Chemother., vol. 34, issued 1990, Shinazi et al, "Activities of 3'-Azido-3'-Deoxythymidine Nucleotide . . .", pp. 1061–1066.
New England J. Med., vol. 322, issued 1990, Cooley et al, "Once Daily Administration of 2',3'-Dideoxyinosine . . .", pp. 1340–1345.
Harris et al, Protein purification methods, published 1989 by IRL Press (New York), pp. 9–10 and 57–60.

*Primary Examiner*—Jeffrey E. Russel
*Attorney, Agent, or Firm*—Rothwell, Figg, Ernst & Kurz

[57] ABSTRACT

A process for obtaining cellular protein having potent anti-HIV activity comprises culturing CD4-positive T cells or myeloid cells in a tissue culture medium under conditions in which the cells are induced to produce and secrete a protein having anti-HIV activity, separating the cells from the culture medium containing the protein and then recovering the protein from the medium, wherein the molecular weight of the protein having anti-HIV activity, as measured by gel filtration analysis, is within the range of about 7,000 to about 12,000 daltons.

9 Claims, 4 Drawing Sheets

PROCESS FOR OBTAINING CELLULAR PROTEIN HAVING ANTI-HIV ACTIVITY

This invention was made with government support under a cooperative agreement UO1 AI 27280 awarded by the National Institutes of Health (NIH). The government has certain rights in the invention.

This is a continuation of application Ser. No. 07/659,564, filed Feb. 22, 1991, now U.S. Pat. No. 5,346,988, which is a continuation-in-part of Ser. No. 07/540,973, filed Jun. 20, 1990, now abandoned.

FIELD OF THE INVENTION

This invention is directed to protein produced and secreted from human CD4-positive T cells or myeloid cells which has potent anti-HIV activity.

BACKGROUND OF THE INVENTION

Acquired Immune Deficiency Syndrome (AIDS) has become a significant public health threat in recent years. A major breakthrough in AIDS research came in 1983–1984 when two groups independently isolated and identified a virus believed to be the causative agent of AIDS. The AIDS virus has been described by several names. It has been known as lymphadenopathy-associated virus (LAV), AIDS-related virus (ARV) and human immunodeficiency virus (HIV). Within the last few years, scientists have discovered that there are at least two distinct viruses, HIV-1 and HIV-2. HIV-1 is the virus originally isolated in 1983 (*Ann. Virol. Inst. Pasteur,* 135E:119–134 [1986]); HIV-2 was isolated by researchers in 1986 (see *Nature,* 326:662 [1987]). As used herein, HIV refers to these viruses generically.

A distinguishing feature of HIV is its selective cytotoxicity for helper T lymphocytes. The virus also infects monocytes/macrophages, B lymphocytes and neural cells. Severe and diverse aberrations of the immune system significantly reduce the host defense against various opportunistic infections, ultimately resulting in host death.

There are a number of cellular proteins secreted by human cells that can regulate the human immune system. These secreted cellular proteins with regulatory activities generally are classified as interleukins or cytokines. The United States Food and Drug Administration (FDA) has approved the use of some of the interleukins/cytokines in clinical trials for the treatment of AIDS. Those approved for clinical trials include interleukin-2 (IL-2), tumor necrosis factor-alpha (TNF-$\alpha$), interferon-alpha (INF-$\alpha$), interferon-beta (INF-$\beta$), interferon-gamma (INF-$\gamma$) and colony stimulating factor for granulocytes and macrophages (GM-CSF). Only the interferons have been shown to possess anti-viral activities before the initiation of the clinical trials. The high doses of interferon required in treatment often give undesirable short-term side effects that precipitate the withdrawal of the interferon treatment. IL-2 has shown no anti-HIV activity, and data available thus far suggest that IL-2 has no significant impact on the reconstitution of CD4-positive helper T cell populations in AIDS patients. Recent reports also have shown that TNF-$\alpha$ and GM-CSF can activate latent HIV in cells maintained in tissue culture. Thus, it is questionable if these agents can be used long-term to treat AIDS patients. There thus remains an urgent need for methods of inactivating the AIDS virus and for the treatment of AIDS.

It therefore is an object of the present invention to provide a novel protein having potent anti-HIV activity. Other objects of the invention will become apparent from the following description and accompanying figures.

SUMMARY OF THE INVENTION

In accordance with the present invention, there is provided a method for obtaining a soluble protein, or proteins, having potent anti-HIV activity, secreted by CD4-positive T cell lines, such as CEM, and by myeloid cell lines, such as U937, cultured in a tissue culture medium. The soluble protein, or proteins, with potent anti-HIV activity, as determined by gel filtration analysis, has a molecular weight of less than about 12,000 and more than about 7,000.

The protein, or proteins, can be recovered from the cell culture by first separating the cells from the medium. The resultant cell-free solution is passed through a 30 kDa molecular sieve and the fraction containing molecules having a molecular weight less than about 30,000 are collected. The preparation has potent anti-HIV activity and can be purified further by adding it to an ion exchange column and eluting with a buffered solution having a linear gradient of 50 mM to 1M sodium chloride. The fractions obtained with 200 mM to 350 mM sodium chloride elution and 600 mM sodium chloride elution possess anti-HIV activity. Gel filtration analysis by fast performance liquid chromatography showed that the fraction with anti-HIV activity has an apparent molecular weight between about 7,000 to about 12,000 daltons.

Detailed Description of the Invention

Figure 1:
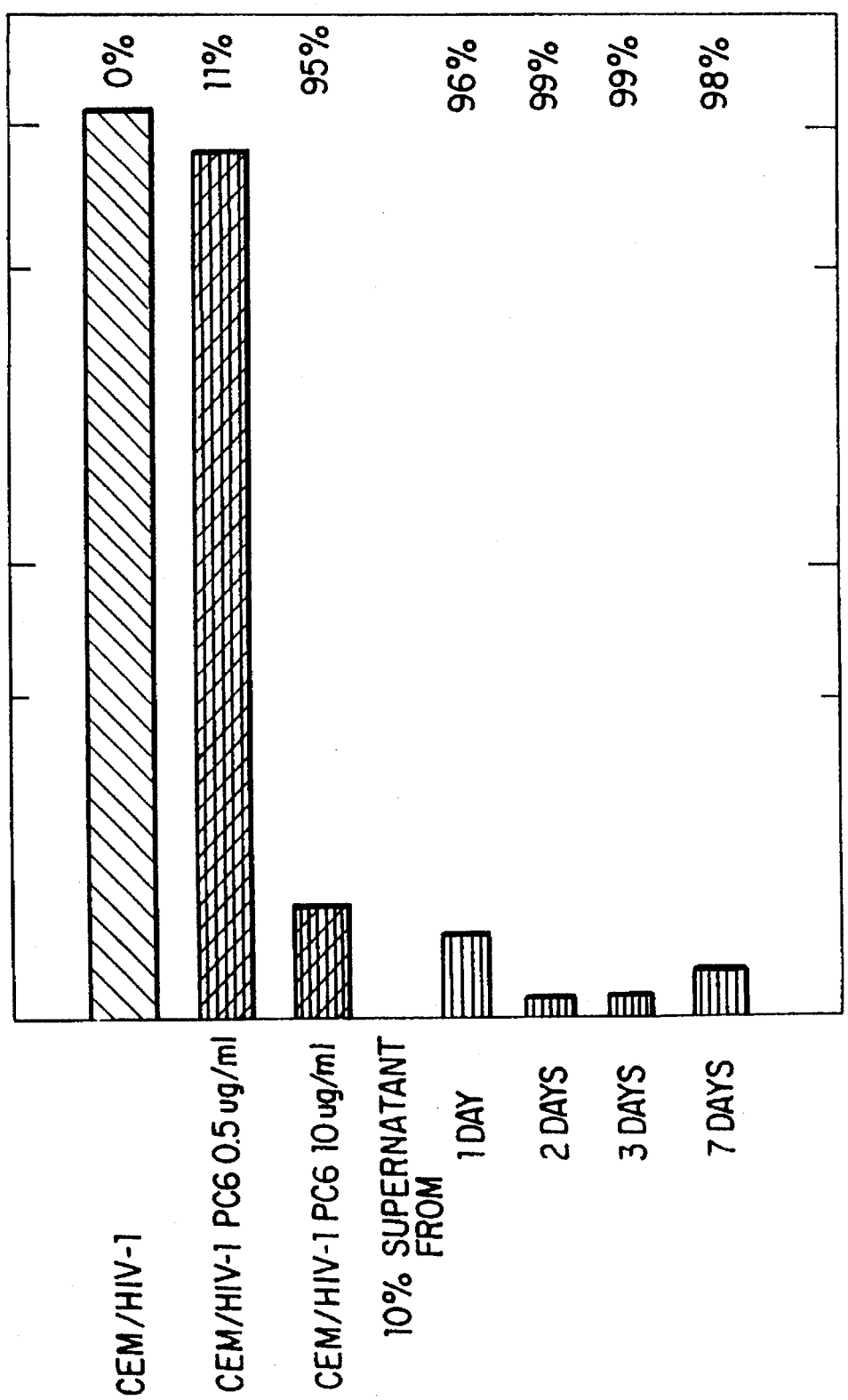
FIG. 1 illustrates in bar graph form the anti-HIV impact of the anti-HIV protein produced by CEM cells activated for 1, 2, 3 and 7 days by PC6.

Suitable starting material for the process of this invention is a CD4-positive T cell line or a myeloid cell line. Examples of CD4-positive T cell lines include CEM, available from the American Type Culture Collection (ATCC), Rockville, Md. accession number CCL119 and H9, available from the National Cancer Institute, Bethesda, Md., accession number 87. Myeloid cell lines include U937 and THP-1, both available from the ATCC as accession numbers CRL 1593 and TIB 202, respectively.

The CD4-positive T cells or myeloid cells are cultured in a tissue culture medium. Generally, any commercially available medium is acceptable to support the growth of the cells, such as RPMI-1640, commercially available from Media Tech., Herndon, Va. Desirably, the medium is supplemented with 5% v/v fetal bovine serum, 100 units/ml penicillin and 100 µg/ml streptomycin.

The culture medium also is modified by the addition of an agent suitable for activating the cells. Examples of useful activating agents include PC6, an extraction from cones of conifer trees described by Lai et al., *AIDS Research and Human Retroviruses,* 6:205–217 (1990), alkaline aqueous extracts from cones of conifer trees (*Anticancer Research*

7:1153–1160 (1987), Klason lignin extracted from conifer cones or pulp waste (*Methods of Wood Chemistry*, B. L. Browning [ed.] Vol. II, p785, Interscience Publishers, New York), alkaline lignin (Tokyo Kasei Organic Chemicals, Tokyo, Japan), de-alkaline lignin (Tokyo Kasei) and lignin sulfonate (Tokyo Kasei).

Generally, the activating agent is added to the tissue culture medium at a concentration of from about 1 to about 30 µg/ml of medium. The cells then are seeded at a concentration ranging from about $1 \times 10^5$ to about $6 \times 10^5$ cells/ml of medium.

The cells then are incubated, generally for a period of about 1 to about 7 days, under conditions which induce the cells to produce one or more proteins having anti-HIV activity. Generally, such conditions include an incubation temperature of about 37° C. and a 100% humidified atmosphere of about 5% carbon dioxide. The length of the incubation time has not been found to be critical; under the conditions generally described above, the cells produce the desired protein or proteins within about 24 hours of the start of the incubation, and high levels of protein still are detected in the medium after 7 days of incubation.

To recover the anti-HIV protein(s), the cells are separated from the aqueous medium. Typically, this is done by centrifugation at, for example, 800×g. The cell pellet is removed from the cell-free aqueous phase. The anti-HIV protein molecules are in the aqueous phase; assays show that when cells infected with the HIV virus are cultured in a cell-free aqueous phase produced in accordance with the steps described above, HIV replication is greatly inhibited in comparison to a similar cell culture grown in a conventional medium. See Example 1, below.

Throughout the remainder of the application, reference will be made to a protein having anti-HIV activity. It is to be recognized, however, that in fact what is produced and secreted by the cells may be a mixture of at least two proteins.

The supernatant containing the anti-HIV protein is passed through a 30 kDa molecular sieve. General conditions include a pressure of 18 psi or 500×g. The anti-HIV protein molecules pass through this sieve but are retained with a 10 kDa molecular sieve. Thus, this is suggestive that the molecular size of the desired molecules is within the range of about 10,000 to about 30,000 daltons. As described below, the molecular weight of the anti-HIV protein is more closely estimated by gel filtration analysis using high performance liquid chromatography to be within the range of about 7000 to about 12000 daltons relative to the gel filtration profile of molecular weight markers. When cells infected with HIV are incubated in the supernatant containing the anti-HIV protein, HIV replication can be inhibited by up to about 98%.

If desired, the anti-HIV protein can be precipitated from the supernatant by adding an aqueous solution of supersaturated ammonium sulfate to a final concentration of at least about 30% by volume at a pH of about 7.0. The precipitate can be recovered by conventional methods. When the protein subsequently is dissolved in a minimal amount of tissue culture, anti-HIV activity can be detected when the preparation is used at a 1/300 dilution in tissue culture medium (see FIG. 1, described in Example 1, below).

Analysis of the anti-HIV protein produced in accordance with this method shows that it is not interleukin-1, interleukin-2, interleukin-3, interleukin-4, interleukin-5, interleukin-6, interleukin-7, interleukin-8, colony stimulation factor for granulocyte and macrophages (GM-CSF), colony stimulation factor for granulocytes, colony stimulation factor for macrophages, interferon-alpha, interferon-beta, interferon-gamma, tumor necrosis factor-alpha, tumor necrosis factor-beta, or transforming growth factor-beta. Specific neutralizing antibodies to each of these factors fails to abrogate the anti-HIV activity of a medium comprising the protein.

If desired, the anti-HIV protein can be purified by ion exchange chromatography. Conventional liquid chromatography, high performance liquid chromatography, or fast performance liquid chromatography can be used. The pH of the anti-HIV protein precipitated by ammonium sulfate is adjusted to be within the range of about 6.5 to about 7.8. The protein then is dissolved in elution buffer. A suitable elution buffer is 10 mM Tris[hydroxymethyl]aminomethane at pH 7.4, 50 mM potassium chloride, 50 mM sodium chloride, 0.1 mM of disodium salt of ethylene diamine tetraacetic acid (EDTA) at pH 7.0 and 0.1 mM dithiothreitol. The solution containing the anti-HIV protein is added to an ion exchange column, such as a DEAE or mono-Q column. The ion exchange column then is eluted with the elution buffer containing a linear gradient of 50 mM–1M sodium chloride. Fractions are collected, and the fraction(s) containing about 200 mM to about 350 mM sodium chloride and the fraction(s) containing about 600 mM sodium chloride contain the anti-HIV protein.

The fraction(s) is analyzed by fast performance liquid chromatography by use of a Superose 12™ 10/30 gel filtration column and an elution buffer. A suitable elution buffer is 25 mM Tris[hydroxymethyl]aminomethane at pH 7.3 and 125 mM of sodium chloride. Fractions are collected, and fractions containing molecules with apparent molecular weights ranging from 1,000 to 30,000 daltons are tested individually for anti-HIV activity. The fraction containing molecules with an apparent molecular weight between 7,000 to 12,000 daltons contain the anti-HIV activity.

The anti-HIV protein in aqueous solution can be stored at 4° C. for up to about 3 months.

The present invention is further illustrated by the following examples, which are not intended to be limiting.

EXAMPLE 1

CEM cells were cultured at $5 \times 10^5$ cells/ml of medium in each of four culture dishes containing 10 ml of RPMI-1640 medium supplemented with 5% fetal calf serum, 100 units/ml penicillin, 100 ug/ml streptomycin and 5 µg/ml PC6.

The cells were incubated at 37° C. for 1, 2, 3 or 7 days in 100% humidified atmosphere of 5% $CO_2$, then the cells were removed by centrifugation at 800×g for 10 minutes. The cell-free supernatant was collected and filtered through a 0.22 µm filter and then tested for anti-HIV activity.

The anti-HIV assay was performed as described by Lai et al., *AIDS Research and Human Retroviruses* 6:205–217 (1990). $5 \times 10^5$ CEM cells were suspended in 1 ml of a virus preparation containing HIV-1 of the N1T strain (*AIDS Research* 1:407 [1985]) at 37° C. for 4 hours.

The infected cells were cultured in 1 ml cultures at $1.5 \times 10^5$ cells/ml in medium (RPMI-1640 medium supplemented with 5% fetal calf serum, 100 units/ml penicillin, 100 µg/ml streptomycin) alone and in medium containing a final concentration of 1 in 10 dilution of each of the cell-free supernatant preparations. Infected cells cultured at $1.5 \times 10^3$ cells/ml in medium either containing 10 µg/ml or 0.5 µg/ml PC6 served as inhibition controls. All test and control cultures were performed in duplicate. After incubation for 5 days at 37° C. in 100% humidified atmosphere of 5% $CO_2$, the amount of HIV-1 present in each culture was assayed by an antigen capture ELISA (Coulter Immunology, Florida) which specifically quantitates the amount of HIV-1 core protein p24. The percent inhibition of HIV replication was calculated as p24 protein in test cultures/p24 concentration in control culture maintained in medium alone.

The results are shown in FIG. 1. As can be seen from the bar graph, there was no noticeable inhibition of HIV-1 replication when the infected CEM cells were grown in culture medium alone and only 11% inhibition when the cells were cultured in medium containing 0.5 µg/ml PC6. Cells cultured in medium containing 10 µg/ml PC6 showed a 95% inhibition in HIV-1 replication. The infected cells cultured in medium containing 10% of the cell-free supernatant showed from 96–99% inhibition of HIV-1 replication.

The publication by Lai et al. referenced above has shown that 3–10 µg/ml of PC6 is required to give a significant inhibition of HIV-1 replication. The experiment described above confirmed these results, as 0.5 µg/ml had little impact on HIV replication but 10 µg/ml did. As the cell-free supernatant was obtained with 5 µg/ml of PC6, the 10% supernatant used in this assay only contained 0.5 µg/ml of PC6. Since 0.5 µg/ml of PC6 when added to the infected cells had no impact on the replication of HIV-1, the anti-HIV impact in the cell-free supernatant could not be attributed to the contaminating (10% of 5 µg/ml) PC6.

EXAMPLE 2

The procedures of example 1 were repeated with the following changes. Production of the anti-HIV protein was carried out as before, except that the activated CEM cells were cultured for 3 days.

The anti-HIV assay was carried out as described in Example 1, except that $5\times10^5$ myeloid cells U937, histiocytic cells (ATCC Accession Number CRL 1593) and $5\times10^5$ THP-1 monocytic cells (ATCC Accession Number TIB 202) were infected with the HIV virus rather than CEM cells, PC6 was used at 5 µg/ml in the inhibition controls, and the anti-HIV protein containing supernatant was used at 10% and at 30%. As before, $1.5\times10^5$ infected cells/ml were cultured in medium alone, medium containing PC6 or medium containing cell-free supernatant.

Figure 2:
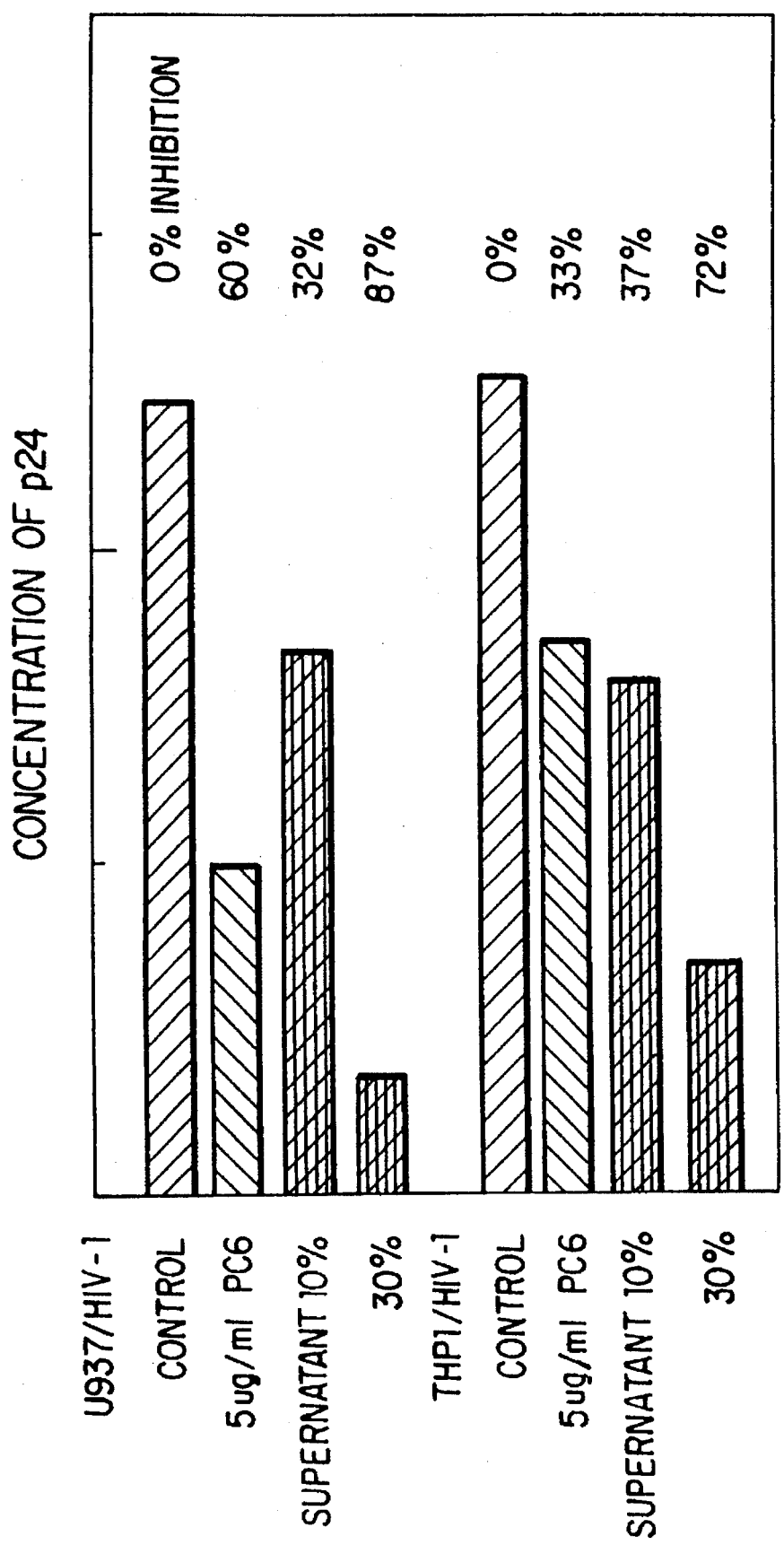
FIG. 2 illustrates in bar graph form the impact of anti-HIV protein on the percent of virus production by U937 histiocytic cells and by THP-1 monocytic cells infected with HIV-1.

The results of the assay are shown in FIG. 2. As can be seen from the bar graph, the replication of HIV-1 in infected cells grown in just the medium is taken as the base against which the amount of replication in cells grown in medium plus other components is measured. U937 and THP-1 cells grown in 5 µg/ml PC6 showed 60% and 33% inhibition of HIV-1 replication, respectively. U937 infected cells grown in medium containing 10% and 30% cell-free supernatant showed 32% and 87% inhibition, respectively. THP-1 infected cells grown in medium containing either 10% or 30% cell-free supernatant showed 37% and 62% inhibition of replication, respectively. The differences noted between growth in medium containing 10% and 30% cell-free supernatant suggests a dose dependent impact on HIV-1 replication.

EXAMPLE 3

$5\times10^2$ cells/ml of CEM cells, obtained from the ATCC, accession number CCL 119, were cultured for three days at 37° C. in 400 ml. RPMI-1640 tissue culture medium supplemented with 5% fetal bovine serum, 100 units/ml of penicillin, 100 µg/ml streptomycin and 10 µg/ml PC6 (obtained from Tampa Bay Research Institute, St. Petersburg, Fla.). The cells were cultivated in 100% humidified atmosphere of 5% $CO_2$. The CEM cells were removed from the culture medium by centrifugation at 800×g for 10 minutes and subsequent removal of the resultant cell pellet. Two liters of supersaturated aqueous ammonium sulfate then were added to the supernatant. A white precipitate formed and was removed from the supernatant by centrifugation at 9000×g for 15 minutes. The precipitate was approximately 7 grams. Most of the protein precipitated was protein from the fetal bovine serum.

The precipitate was dissolved in 10 ml of an aqueous elution buffer containing 10 mM Tris[hydroxymethyl]aminomethane, 50 mM potassium chloride, 50 mM sodium chloride, 0.1 mM disodium salt of EDTA and 0.1 mM dithiothreitol. The solution was added to a DEAE column having a pH of 7.4 and eluted with 500 ml of the elution buffer having a linear salt gradient of 50 mM to 1M sodium chloride. The sodium chloride linear gradient was prepared with a gradient maker (Isolab, Akron, Ohio) with eluant A the elution buffer with 50 mM sodium chloride and eluant B the elution buffer with 1M sodium chloride.

Fourteen fractions, each containing about 10 ml of eluate, were collected. The two fractions (numbers 6 and 7) obtained with 200 mM to 350 mM sodium chloride eluant were pooled and then dialyzed at 4° C. for 4 hours against 4 changes of 500 ml of the elution buffer containing 50 mM sodium chloride to desalt the fractions.

Figure 3:
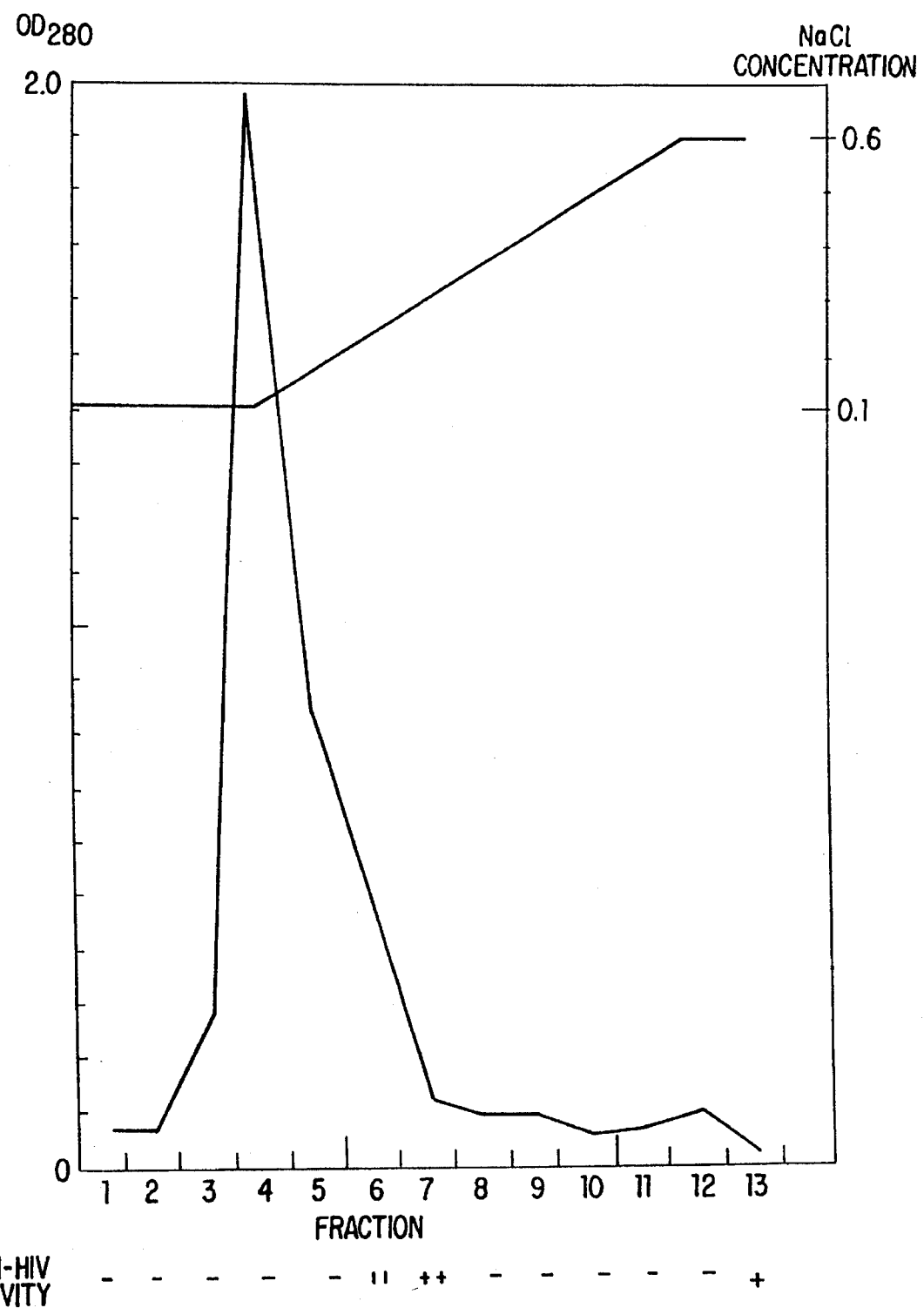
FIG. 3 is a graph illustrating the elution profile of the anti-HIV protein from a DEAE cellulose column.

The elution profile and the anti-HIV activity of the eluates are shown in FIG. 3. Fractions 1–4 were eluted with 0.1M sodium chloride. Fractions 6–12 were eluted with a linear gradient of 0.1–0.6M sodium chloride with an increment of approximately 0.08M sodium chloride per fraction. Fractions 13–14 14 were eluted with 0.6M sodium chloride. As can be seen from FIG. 3, fractions 3–6 contained high concentrations of proteins detected as a single peak absorption at 280 nm ($OD_{280}$) ultraviolet wavelength with a photometer (Beckman Instruments). Minor peaks of proteins also were found in fractions 9 and 12.

The anti-HIV activity in each fraction was assayed in accordance with the procedure described by Lai et al., above. $5\times10^5$ cells CEM cells were infected with 1 ml of a virus preparation containing HIV-1 of the N1T strain. The infected cells were cultured in 1 ml cultures at $1.5\times10^5$ cells/ml in RPMI-1640 medium (supplemented with 2% new born calf serum, 100 units/ml penicillin, 100 µg/ml streptomycin) alone and in medium containing a final concentration of 1 in 10, 1 in 30, or 1 in 100 dilution of each of the fractions obtained from the column above. Infected cells cultured at $1.5\times10^5$ cells/ml in medium containing 5 µg/ml and 0.5 µg/ml PC6 served as inhibition controls. All test and control cultures were performed in duplicate. After incubation for 5 days at 37° C. in 100% humidified atmosphere of 5% $CO°2°$, the cell-free supernatant from each of the cultures was collected. The amount of HIV-1 present in each of the supernatants was assayed by an antigen capture ELISA as described in Example 1. A fraction was considered to possess anti-HIV activity (denoted ++ as shown in FIG. 3) if it inhibited HIV-1 replication by 90% when used at a final dilution of 1 in 30. A fraction was considered to possess some anti-HIV activity (denoted by + in FIG. 3) if it inhibited HIV-1 replication by 50–89% when used at a final dilution of 1 in 30. A fraction was considered not to have anti-HIV activity (denoted by − in FIG. 3) if it inhibited HIV-1 replication by less than 50% when used at the final dilution of 1 in 30.

As can be seen from FIG. 3, fractions 6 and 7 had anti-HIV activity. Since fraction 7 had a very low protein concentration as detected by ultraviolet absorption at 280 nm that detected μg per ml of proteins, the results suggest that the anti-HIV protein in fraction 7 is extremely potent. Fraction 13 also had anti-HIV activity, although it was less than that shown by fractions 6 and 7.

EXAMPLE 4

A preparation (Bio-Rad) containing the following molecular markers: Thyroglobulin (670,000 dalton), gamma globulin (158,000 dalton), ovalbumin (44,000 dalton), myoglobin (17,000 dalton) and vitamin B-12 (1350 dalton) was analyzed with a Superose 12™ 10/30 gel filtration column (Pharmacia) and eluted by fast performance liquid chromatography at one ml/min with the elution buffer having 25 mM Tris[hydroxymethyl]aminomethane at pH 7.3 and 125 mM of sodium chloride. Elution profile of the 158 kilodalton gamma globulin, 44 kilodalton ovalbumin, 17 kilodalton myoglobulin and 1.35 kilodalton vitamin B-12 is given in FIG. 4A, top graph.

Fraction 7 containing high anti-HIV activity eluted from the DEAE-cellulose column in Example 3 was dialyzed overnight at 4° C. against a buffer containing 25 mM Tris[hydroxymethyl]aminomethane at pH 7.3 and 125 mM of sodium chloride. Five ml of the dialyzed preparation were added to a Superose 12™ 10/30 gel filtration column (Pharmacia) and eluted by fast performance liquid chromatography at one ml/min with the elution buffer having 25 mM Tris[hydroxymethyl]aminomethane at pH 7.3 and 125 mM of sodium chloride under the same experimental conditions. Six 1 ml fractions were collected at 1 minute intervals between retention time of 35 min to 40 min. One 2 ml fraction corresponding to retention time of 41 and 42 min, and seven 1 ml fractions corresponding to retention time 43 to 49 minutes were collected. Relative to the retention time of the molecular markers shown in the top graph of FIG. 4A, molecules with retention time of 35 to 49 min should have an apparent molecular weight ranging from 30,000 to 1000 daltons.

Figure 4A:
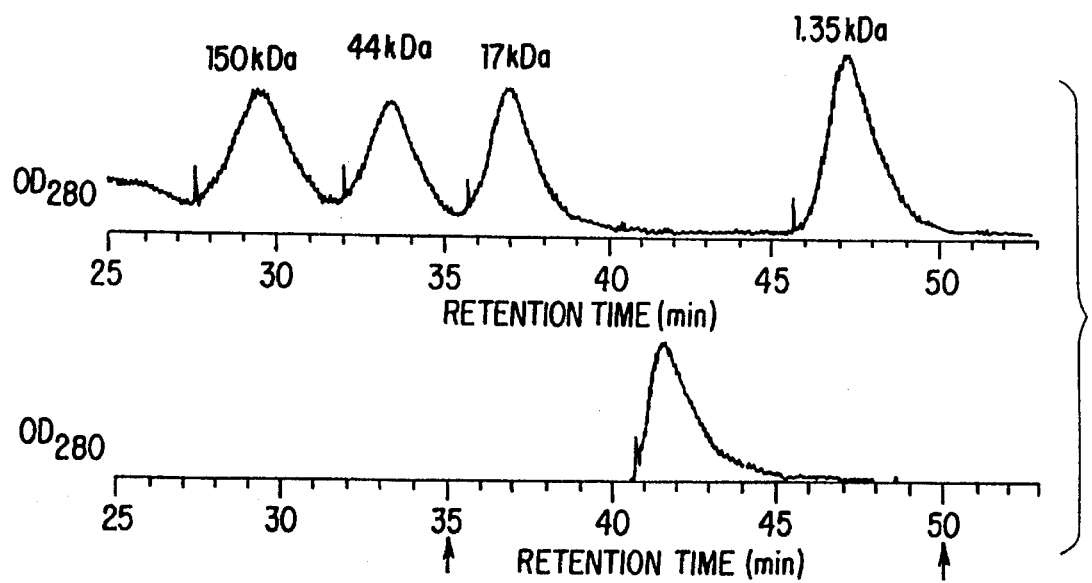
FIGS. 4A an B are a graph illustrating the fast performance liquid chromatographic gel filtration profile of the anti-HIV fraction from the DEAE cellulose column. It shows that the fraction containing molecules with a molecular weight between about 7,000 to about 12,000 daltons had the highest anti-HIV activity.
Figure 4B:
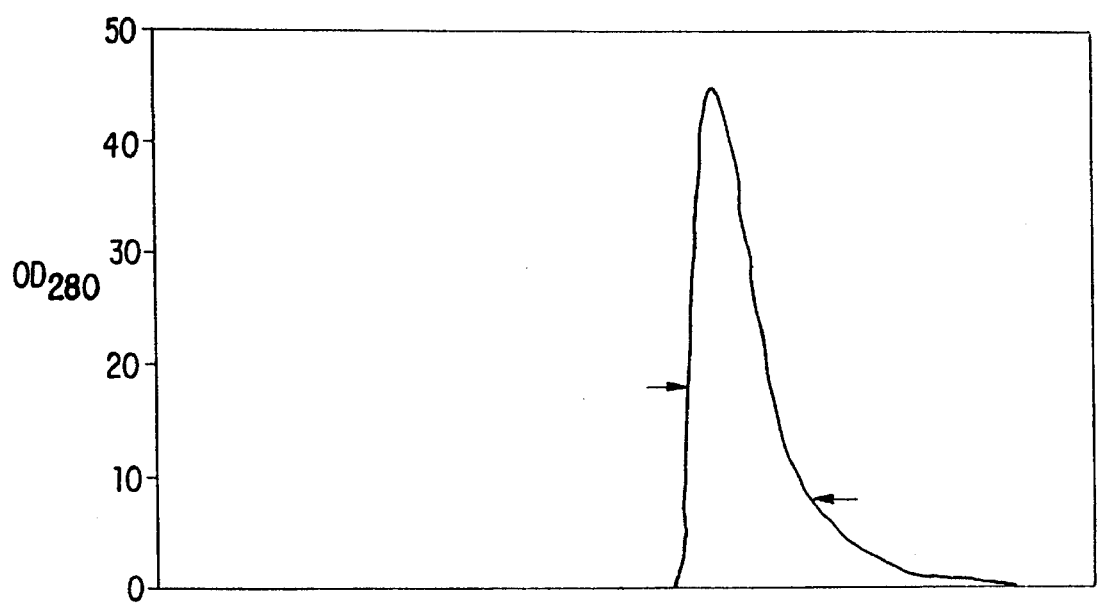

The anti-HIV activity in each of the collected fractions was assayed as described by Lai et al. (*AIDS Research and Human Retroviruses* 6:205–217, 1990). Briefly, CEM cells ($5\times10^5$ cells/ml of virus) were infected with a virus preparation containing HIV-1 of the NIT strain (*AIDS Research* 1:407, 1985). The infected cells were cultured in growth medium (RPMI-1640 medium supplemented with 5% fetal calf serum and antibiotics) and 1 in 30 or 1 in 100 dilution of each of the fractions collected from the column above. Infected cells cultured in growth medium alone served as control. After incubation for 5 days at 37° C., the concentration of HIV-1 in culture was assayed by an ELISA to HIV-1 p24 protein. Anti-HIV activity was detected only in the fraction (area between the two arrows in FIG. 4B) corresponding to molecules possessing a retention time of 41 and 42 minutes shown in the bottom graph of FIG. 4A. Thus, the apparent molecular weight of the anti-HIV protein estimated relative to the elution profile and the retention times of the molecular markers shown in the top graph of FIG. 4A is between 7,000 to 12,000 daltons.

We claim:

1. A method for inhibiting HIV replication in vitro which comprises contacting cells infected with HIV with an HIV-inhibiting amount of a protein having a molecular weight of about 7,000 to about 12,000 daltons as determined by gel filtration analysis, the protein obtainable by a method which comprises:

(a) culturing CD-4 positive T cells or myeloid cells in a tissue culture medium comprising an agent to activate the cells, (b) incubating said tissue culture medium for a period of time sufficient to induce the cells to produce and secrete at least one protein having anti-HIV activity;

(c) separating the cells from the culture medium containing the protein having anti-HIV activity; and (d) recovering the protein from the medium.

2. A method in accordance with claim 1, wherein the activating agent comprises PC6, alkaline lignin, de-alkaline lignin or lignin sulfonate.

3. A method in accordance with claim 1, wherein the cells being cultured in step (a) are CEM cells.

4. A method in accordance with claim 1, wherein the cells being cultured in step (a) are U937 or THP-1 cells.

5. A method in accordance with claim 1, wherein the cells in step (a) are seeded in the culture medium at a concentration of about $1\times10^5$ cells/ml to about $6\times10^5$ cells/ml and the activating agent is provided at a concentration of from about 1 μg/ml to about 30 μg/ml.

6. A method in accordance with claim 1, wherein the medium further comprises 5% v/v fetal bovine serum, 100 units/ml penicillin and 100 μg/ml streptomycin.

7. A method in accordance with claim 2, wherein the activating agent is PC6.

8. A method in accordance with claim 7, wherein the HIV infected cells are cultured in a medium comprising from 1 to 30 μg/ml of the activating agent.

9. A method in accordance with claim 8, wherein HIV replication is inhibited by about 95–99%.

* * * * *